United States Patent [19]

Ryan

[11] 4,216,773
[45] Aug. 12, 1980

[54] DISPOSABLE DIAPER WITH CENTER FOLDED EDGES

[75] Inventor: A. Sensor Ryan, Tacoma, Wash.

[73] Assignee: Weyerhaeuser Company, Tacoma, Wash.

[21] Appl. No.: 25,439

[22] Filed: Mar. 30, 1979

[51] Int. Cl.² ............................................. A61F 13/16
[52] U.S. Cl. ................................................. 128/284
[58] Field of Search ............... 128/284, 286, 287, 288, 128/289

[56] References Cited

U.S. PATENT DOCUMENTS

| | | | |
|---|---|---|---|
| 1,490,303 | 4/1924 | Woody | 127/284 |
| 1,694,161 | 12/1928 | Budwig et al. | 128/284 |
| 2,122,417 | 7/1938 | Fridolph | 128/284 |
| 2,224,518 | 12/1940 | Lakritz | 128/284 |
| 2,788,003 | 4/1957 | Morin | 128/284 |
| 2,866,460 | 12/1958 | Tomlinson | 128/284 |
| 3,176,688 | 4/1965 | Tschappat | 128/284 |
| 3,461,871 | 8/1969 | Foote | 128/284 |
| 3,794,033 | 2/1974 | Ryan | 128/284 |

Primary Examiner—C. Fred Rosenbaum

[57] ABSTRACT

A disposable diaper that is better fitting and has the absorbent material more advantageously located is made by cutting two longitudinal slits in the front end of a generally rectangular absorbent pad. Flaps are generated by a fold line originating on the edges of the pad, at or near the rear corners, and projected to intersect the adjacent slits at or near their inner ends. The flaps are folded inwardly to create a generally Y-shaped diaper having multiple layers of absorbent material in the area of heaviest wetting.

6 Claims, 14 Drawing Figures

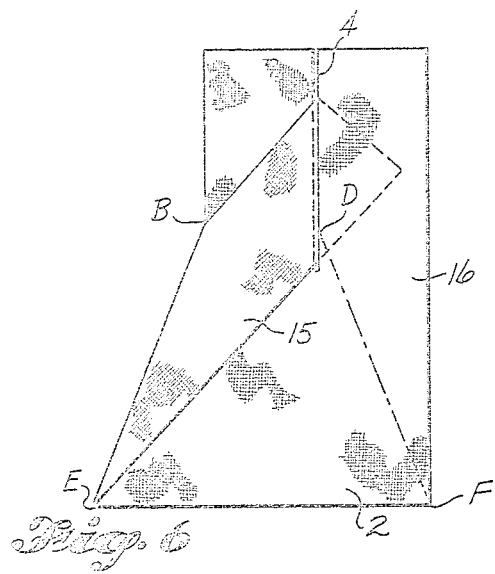
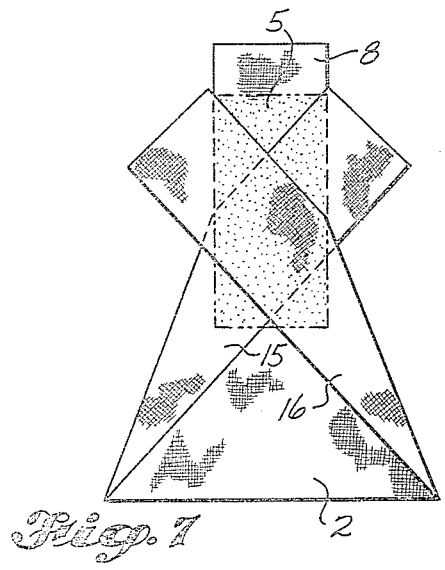
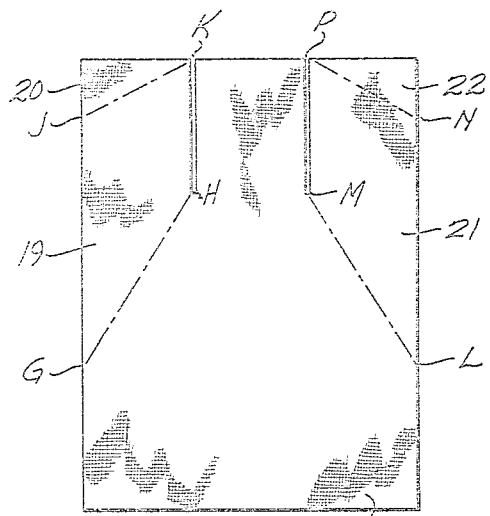
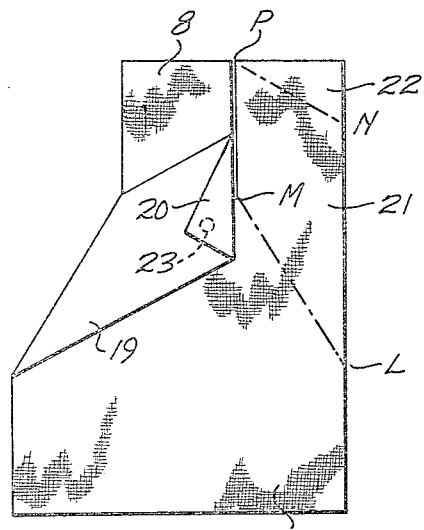
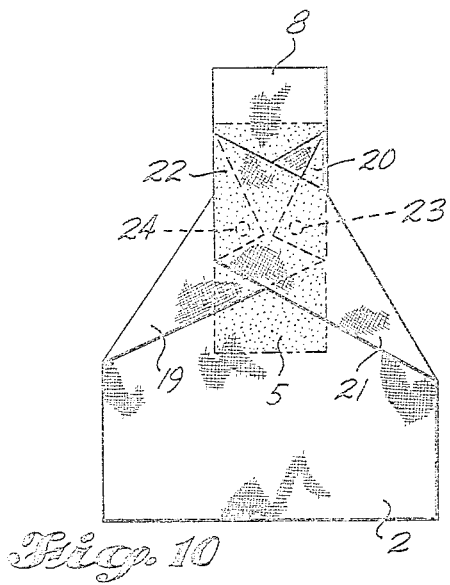

DISPOSABLE DIAPER WITH CENTER FOLDED EDGES

BACKGROUND OF THE INVENTION

This invention relates generally to a disposable diaper and, more particularly, to an improved disposable diaper having a construction with increased absorbent material in the area of maximum wetting.

All practical disposable diaper designs have been based on the use of a flat absorbent pad of relatively uniform thickness. The use of a rectangular pad poses two problems; one of fit and one of placement of absorbent material where it is most needed. These problems are in a way related and pose a dilemma. With a standard rectangular pad, the fit problem is caused by an excess of material in the crotch area, yet this is the very location where extra material is needed for moisture absorption. In effect, this excess is displaced to the edges where it creates extra bulk when it is really needed in the center section for absorbency.

The above problem has had extensive consideration, as is shown by the voluminous patent literature. Examples of patents showing either a built-up or contoured crotch area, or both, are those to Woody, U.S. Pat. Nos. 1,490,303; Budwig et al., 1,694,161; Fridolph, 2,122,417; Morin, 2,788,003; Tomlinson, 2,866,460; Tschappat, 3,176,688; Foote, 3,461,871; and others.

Disposable diapers are made in huge quantities and sold at a very low unit cost. As such, they are a highly competitive product. There is extreme pressure to develop the simplest possible designs and manufacturing techniques compatible with supplying a high quality product to the marketplace.

One such improved design is shown in applicant's earlier patent, U.S. Pat. No. 3,794,033. In this design, two symmetrically opposite cuts were made in the sides of the diaper. These began at or near a front corner and angled inwardly, about ¼ to ⅓ of the distance toward the opposite rear corner. This resulted in the formation of two triangular flaps that were folded inwardly so as to overlap in the crotch area and give a generally hourglass-shaped configuration. A dual purpose was accomplished; a form fitting construction was created at the crotch area and a double or triple thickness of absorbent material was provided at the area where it was most needed.

Unfortunately, the designs shown in U.S. Pat. No. 3,794,033 are hard to manufacture on high speed equipment because the angling cuts from the edge are difficult to place accurately and the slitting equipment to make them presents a severe maintenance problem. The basic design also suffers somewhat since most versions do not place as much additional padding in the most critical wetting area as is desired.

Accordingly, one object of the present invention is to offer a disposable diaper with additional absorbent material positioned at the most critical wetting area.

Another object is to present a contoured diaper that is readily applied and is more comfortable to wear.

A further object is to provide a diaper with a built-up crotch portion that lends itself to simple and economical manufacturing techniques.

These and other objects of the invention will become apparent upon reading the following specifications in conjunction with the attached drawings.

SUMMARY OF THE INVENTION

The present invention is practiced by modifying a generally rectangular flat absorbent diaper pad. This is accomplished by first making a pair of slits in the front end of the diaper pad. These are generally parallel to each other and to the edges of the diaper, and will be about 10% to 20% of the distance from each edge to the longitudinal centerline. They will extend from about 20% to 50% of the length of the pad. In one version of the invention, they will be of equal length and in another version they will be unequal. A pair of longitudinally symmetrical flaps are thus formed. These are turned inward along lines defined approximately by the bottom of the slits and a point at or near the corresponding back corners of the diaper so as to lie across each other in X-fashion over the front one-half of the diaper. Depending on the angle of the fold, it may be necessary to tuck the first flap through the opposite slit before making the second fold. The folded flaps create a diaper that is narrower at the front, with a multiple thickness of absorbent material in the critical are of maximum wetting. The folded pad may then be enclosed within an envelope comprising an impermeable backing film and a permeable upper material.

BRIEF DESCRIPTION OF THE DRAWINGS

FIG. 6 is a plan view showing the first overfold of a second version of a folded pad.

FIG. 7 is a similar plan view showing the completely folded product of the second version.

FIG. 8 is a plan view of the inner surface of a rectangular flat absorbent pad having a pair of equal length parallel slits therein.

FIG. 9 is a similar plan view of a third version showing the first flap folded over and having the tip of the flap folded back upon itself to place additional absorbent material in the area of maximum wetting.

FIG. 10 is a similar plan view showing the fully folded third version of the invention.

DESCRIPTION OF THE PREFERRED EMBODIMENT

Figure 1:
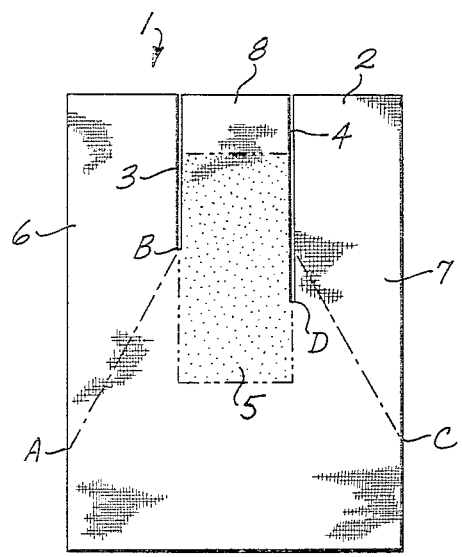
FIG. 1 is a plan view of the inner surface of a rectangular flat absorbent pad having a pair of unequal length parallel slits therein.
Figure 2:
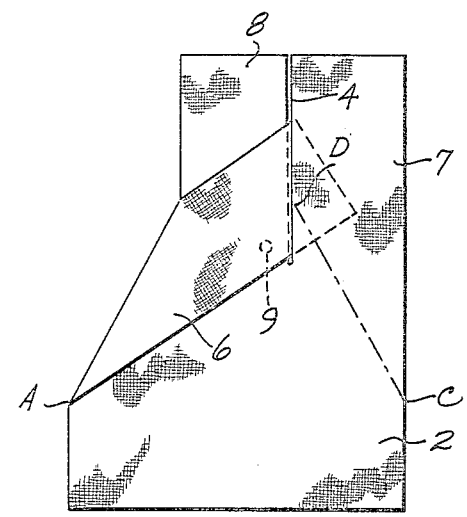
FIG. 2 is a similar plan view of one version showing the first overfold of one of the flaps.
Figure 3:
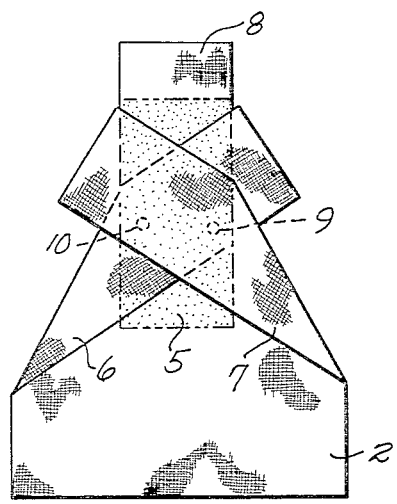
FIG. 3 is a similar plan view of the same version showing both flaps folded.
Figure 4:
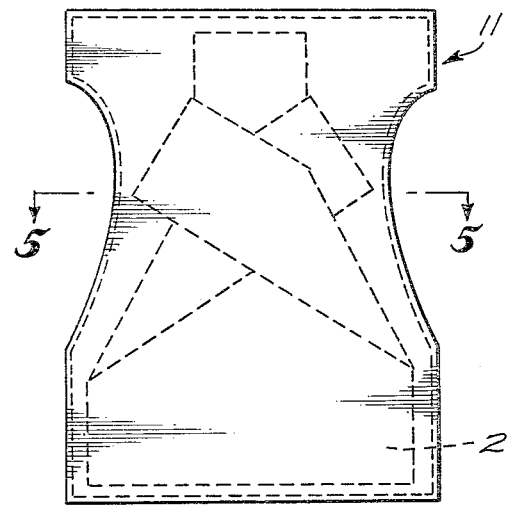
FIG. 4 is a plan view showing the folded pad enclosed within a conventional envelope for diapering an infant.
Figure 5:
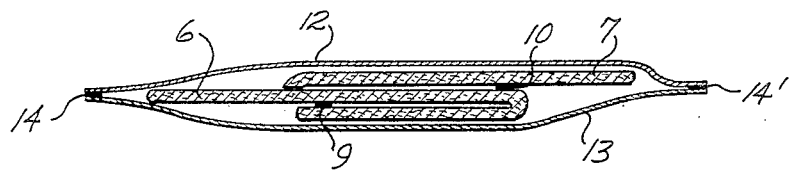
FIG. 5 is a section through 1—1 of FIG. 4.

The finished disposable diapers constructed according to the present invention are manufactured from a rectangular flat pad having an inner absorbent layer normally comprised of fluffed cellulosic pulp, an outer moisture impermeable layer normally comprised of a polyethylene film, and an inner pervious layer comprising a nonwoven tissue extending over the inner absorbent layer. The fluffed cellulosic pulp is normally contained within thin layers of tissue that give mechanical integrity. This construction for a disposable diaper is well known in the art and is depicted in many issued patents. For this reason, the present drawings do not specifically show the layered construction in detail. The functions of each of the layers is also well known, but will be briefly mentioned here for clarification of the present invention. The moisture impermeable layer, located on the outside during use, serves to contain moisture within the bounds of the absorbent pad. The fluffed cellulosic layer operates to hold the majority of the moisture while the pervious nonwoven tissue layer acts to contain the inner absorbent layer within its intended bounds and also to better allow distribution of liquid over a larger area of the absorbent cellulosic layer.

In forming a disposable diaper according to the present invention, the first step is to make the generally rectangular flat pad 1 so that its inner surface 2, that is, the surface which will be adjacent the infant's skin, can be divided into appropriate forming lines. For purposes of this description, reference to the flat pad 1 will be taken to mean the absorbent layer. After the pad is formed into its appropriate shape according to the present invention, the other layers can then be applied to finish the construction.

In manufacturing the disposable diaper of the present invention from the rectangular flat pad 1, a pair of generally parallel slits 3, 4 are cut inwardly from the front end of flat pad 1. In some versions of the invention slits 3 and 4 will be of equal length while in other versions one will be represented as being about 25% longer than the other. The purpose for this will soon become apparent. The longitudinal slits are generally located about 10% to 20% of the distance from each edge of the diaper to the longitudinal centerline. Normally they will be about one-sixth of the distance from the edge to the longitudinal centerline of the diaper. The slits will vary in length from 20% to 50% of the total longitudinal dimension of the diaper. Normally, they will more usually be in the range from one-third to one-half of the length of the diaper.

Before the describing the invention further, it will be useful to explain the concept of a "critical wetting area". This is the area of a diaper which receives the urine flooding from either male or female infants. It is also the area where much of the moisture remains, even though some is transmitted to the ends and edges. The critical wetting area comprises approximately the center one-third of the diaper in lateral dimension and from about one-eighth to five-eighths of the front-to-back length of the diaper. This is the area where it is desirable to have extra thicknesses of padding for increased absorption.

Referring now to FIGS. 1 to 5, a standard flat rectangular pad 1, having an inner surface 2, is slit longitudinally as at 3 and 4. The critical wetting area, where is desired to maximize location of absorbent material, is shown as 5. In the course of manufacture first flap 6 is folded along line AB and tucked through elongated slot 4. The second flap 7 is then folded along line CD so as to overlie flap 6. The intersection of line CD with slit 4 is about 25% above its inner end so as to produce a pair of longitudinally symmetrical flaps. Flaps may be secured if desired by glue spots 9 and 10. A front portion 8 of the pad extends up the abdomen of the infant. The folded pad may now be enclosed within a conventional envelope 11 which consists of an upper permeable nonwoven tissue layer 12 and lower impermeable polyethylene film 13. The two layers are bonded together at the edges by a hot melt adhesive 14, 14'.

As a first alternative construction, the rectangular pad 1, slit as shown in FIG. 1, may be folded along score lines EB and FD as shown in FIGS. 6 and 7. Again, first flap 15 is tucked through slit 4 before the second flap 16 is overloaded. Somewhat more efficient coverage in the critical wetting area is achieved by the configuration shown in FIGS. 6 and 7. As an example, in a standard 30.5 by 40.6 cm diaper pad, when cut 3 is 15.6 cm long and cut 4 is 19.6 cm long, each cut being located 10.2 cm from its respective edge, 89% of the critical wetting area will have at least double pad thickness and 39% will have a triple pad thickness.

Figure 11:
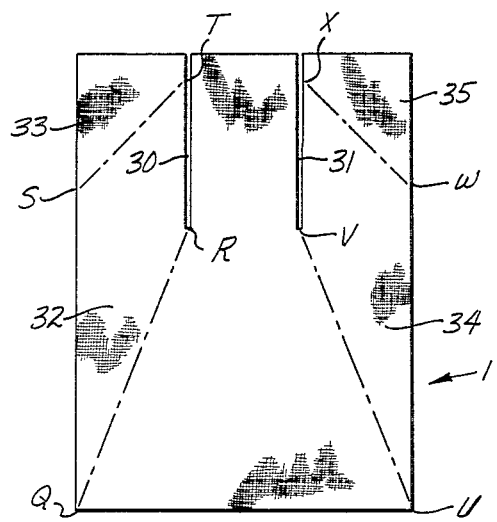
FIG. 11 is a plan view of a rectangular pad similar to FIG. 8 showing a fourth folding pattern of the present invention.
Figure 12:
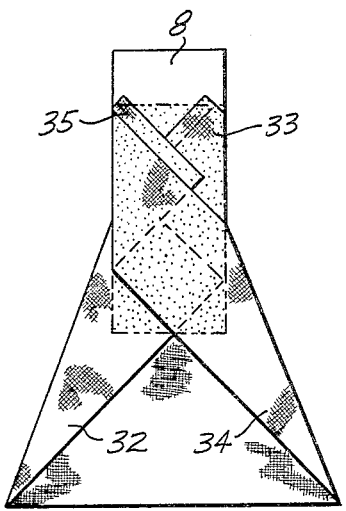
FIG. 12 is a similar plan view of the fully folded diaper of the fourth version.

Another alternative method of folding that will even give quadruple pad thickness over a portion of the critical wetting area is shown in FIGS. 8 and 9. In this case the two longitudinal cuts 17 and 18 are of equal length. The first fold of flap 19 is made along line GH. A second fold of subflap 20 is then made along line JK. These would normally be bonded down by glue spots 23. After these folds, flap 21 is folded along line LM and subflap 22 along line NP. These would then be bonded down with glue spots 24 as shown in FIG. 10. In this illustration subflap 22 is folded the opposite direction from subflap 20 so that it is not visible in the final product. This is not essential and does not affect performance but has been done merely for aesthetic reasons. A similar modification can be made to the general configuration shown in FIG. 6. In this case the absorbent pad, shown now in FIG. 11, has equal length slits 30 and 31. The first flap 32 is folded along line QR and subflap 33 is next folded along line ST. Second flap 34 is then folded along line UV and subflap 35 along line WX. Again for aesthetic reasons, as shown in FIG. 12, the second subflap could be folded in the opposite direction to the first so that it was largely hidden in the final configuration. In some cases, manufacturing considerations may make it more desirable to fold the subflaps before the main flaps are folded. This, of course, does not change the final product in any way.

Figure 13:
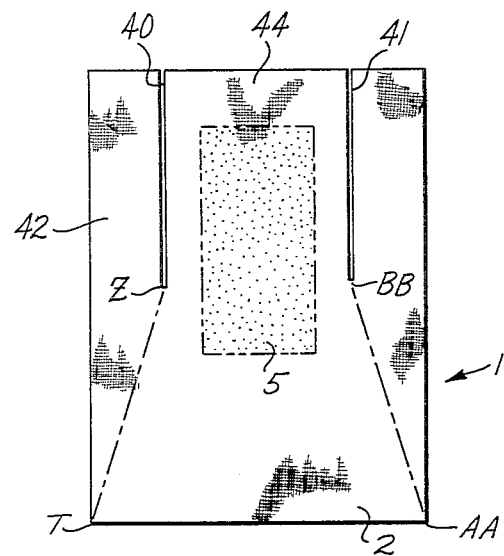
FIG. 13 is a plan view of an absorbent rectangular pad having more widely spaced slits than the previous versions.
Figure 14:
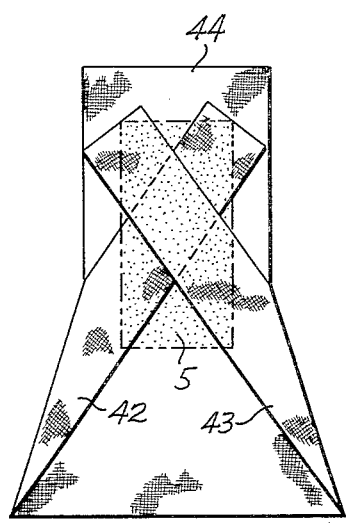
FIG. 14 is a similar plan view showing both flaps of a fifth version overfolded into position.

One more variation is shown in FIGS. 13 and 14. In this case the longitudinal slits would be placed to give a slightly narrower flap than those shown in the previous illustrations. This configuration, which does not give quite as good multiple coverage of the critical wetting area, is easier to manufacture than the diapers shown in FIG. 3 or FIG. 6. This is because the first flap does not have to be tucked through the slit on the opposite side before the second flap can be folded. In this illustration, score lines 40 and 41 are made in pad 1. First flap 42 is folded along line YZ and second flap 43 along line AABB to give the diaper shown in FIG. 14. This configuration may also be advantageous in some circumstances because of the greater width of front section 44.

The longitudinal end slits can most conveniently be made by a rotary cutter which may also simultaneously sever the formed batt into individual pads. In this case the cutting knives would be in a simple circumferential orientation on the cutting roll. Knives of this type are very much easier to manufacture and sharpen than the helical knives that are required for the configurations shown in my eariler patent U.S. Pat. No. 3,794,033. In a commodity product such as disposable diapers a difference of this type can often mean economic success or failure of the product.

It should be obvious to those skilled in the art that many departures can be made from the examples given that would still be included within the spirit of the invention. As one instance, the invention has been described with the left hand flap always being folded first and the right hand slit being the longer in the case of unequal length. It should be obvious that the opposite situation would be fully equivalent. It is understood that the attached claims include within their scope all such changes and modifications.

What is claimed is:

1. A diaper pad having increased absorbent material in the area of maximum wetting, the pad constructed from a generally rectangular piece of absorbent material, wherein the improvement comprises;

a pair of longitudinal slits generally parallel to each other and to the sides of the pad, the slits extending from the front end toward the back end of the pad;

a pair of flaps defined by fold lines symmetrical about a longitudinal axis, the fold lines originating on opposite sides of the pad at or near the corners of the back end of the pad and extending generally to the inner ends of the adjacent slits;

the flaps being folded over the surface of the pad to lie in substantially the same plane, thereby defining a generally Y-shaped diaper having a central portion with at least three layers of absorbent material over part of the maximum wetting area.

2. The diaper of claim 1 wherein the slits extend from 20% to 50% of the total length of the diaper and each slit originates inward from the edge from 10% to 20% of the distance from the edge to the longitudinal centerline.

3. The diaper of claim 2 in which the slits are of unequal length and the fold lines are generated by projecting a first fold line from at or near a first rear corner generally through the end of the shorter slit and then generating an opposite fold line symmetrical about a longitudinal axis, the opposite fold line intersecting its corresponding longer slit substantially above the inner end of the slit.

4. The diaper of claim 3 in which the flap defined by the first fold line is folded over first, this flap being tucked through the longer slit before the flap defined by the second fold line is folded over.

5. The diaper of claim 2 wherein any portion of a folded flap that extends beyond the line defining the opposite slit is folded back upon itself to add additional pad thickness in the critical central portion.

6. The diaper of claim 1 wherein the flaps are bonded in place by spots of adhesive.

* * * * *

UNITED STATES PATENT AND TRADEMARK OFFICE
CERTIFICATE OF CORRECTION

PATENT NO. : 4,216,773
DATED : August 12, 1980
INVENTOR(S) : A. Sensor Ryan

It is certified that error appears in the above-identified patent and that said Letters Patent are hereby corrected as shown below:

In column 2, line 22, "are" should read --area--

In column 3, line 47, delete second word "the"

In column 4, line 12, "overloaded" should read --overfolded--

Signed and Sealed this

Tenth Day of February 1981

[SEAL]

Attest:

Attesting Officer

RENE D. TEGTMEYER

Acting Commissioner of Patents and Trademarks